US012290613B2

(12) United States Patent
Daniel et al.

(10) Patent No.: US 12,290,613 B2
(45) Date of Patent: May 6, 2025

(54) MICRONIZED COMPOSITIONS COMPOSED OF BONE GRAFTS AND METHODS OF MAKING AND USING THE SAME (71) Applicant: MiMedx Group, Inc., Marietta, GA (US)

(72) Inventors: John Daniel, Kennesaw, GA (US); Randall Spencer, Kennesaw, GA (US); Robert Tofe, Kennesaw, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

(21) Appl. No.: 13/647,308

(22) Filed: Oct. 8, 2012

(65) Prior Publication Data
US 2014/0017280 A1 Jan. 16, 2014

Related U.S. Application Data (60) Provisional application No. 61/543,934, filed on Oct. 6, 2011.

(51) Int. Cl.
A61L 27/36 (2006.01)

(52) U.S. Cl.
CPC ....... A61L 27/3604 (2013.01); A61L 27/3608 (2013.01); A61L 2400/06 (2013.01); A61L 2430/02 (2013.01); A61L 2430/24 (2013.01)

(58) Field of Classification Search
CPC ............. A61L 27/3604; A61L 27/3608; A61L 2400/06; A61L 2430/02; A61L 2430/24; A61P 1/02; A61P 19/02; A61P 19/08; A61P 29/00; A61P 43/00
See application file for complete search history.

(56) References Cited

U.S. PATENT DOCUMENTS

| | | | |
|---|---|---|---|
| 2,694,914 A | 11/1954 | Glover, Jr. | |
| 4,564,368 A | 1/1986 | Sawyer et al. | |
| 4,745,771 A | 5/1988 | Linner et al. | |
| 4,968,325 A | 11/1990 | Black et al. | |
| 5,118,867 A | 6/1992 | Bahrmann et al. | |
| 5,284,655 A * | 2/1994 | Bogdansky et al. | 424/422 |
| 6,030,635 A * | 2/2000 | Gertzman et al. | 424/423 |
| 6,387,369 B1 | 5/2002 | Pittenger et al. | |
| 6,936,271 B1 * | 8/2005 | Oliver | A61L 27/24 424/426 |
| 7,311,904 B2 | 12/2007 | Hariri | |
| 7,311,905 B2 | 12/2007 | Hariri | |
| 8,067,044 B2 | 11/2011 | Henry et al. | |
| 8,153,162 B2 | 4/2012 | Tseng et al. | |
| 8,323,701 B2 | 12/2012 | Daniel et al. | |
| 8,357,403 B2 | 1/2013 | Daniel et al. | |
| 8,372,439 B2 | 2/2013 | Daniel et al. | |
| 2002/0123141 A1 | 9/2002 | Hariri | |
| 2002/0160510 A1 | 10/2002 | Hariri | |
| 2003/0032179 A1 | 2/2003 | Hariri | |
| 2003/0187515 A1 | 10/2003 | Hariri et al. | |
| 2004/0028711 A1 | 2/2004 | Uchida et al. | |
| 2004/0048796 A1 | 3/2004 | Hariri et al. | |
| 2006/0140913 A1 | 6/2006 | Bhatia | |
| 2006/0166361 A1 | 7/2006 | Seyda et al. | |
| 2006/0210532 A1 | 9/2006 | Carmeliet et al. | |
| 2007/0020225 A1 | 1/2007 | Abramson et al. | |
| 2007/0021762 A1 | 1/2007 | Liu et al. | |
| 2007/0031471 A1 * | 2/2007 | Peyman | A61L 27/3604 424/427 |
| 2007/0071740 A1 | 3/2007 | Tseng et al. | |
| 2007/0071828 A1 | 3/2007 | Tseng et al. | |
| 2007/0202189 A1 | 8/2007 | Ahlfors | |
| 2007/0248575 A1 * | 10/2007 | Connor | A61K 35/32 424/93.7 |
| 2007/0299043 A1 | 12/2007 | Hunter et al. | |
| 2008/0046095 A1 | 2/2008 | Daniel | |
| 2008/0050347 A1 | 2/2008 | Ichim | |
| 2008/0069895 A1 | 3/2008 | Liu et al. | |
| 2008/0131966 A1 | 6/2008 | Hariri | |
| 2008/0181935 A1 | 7/2008 | Bhatia et al. | |
| 2008/0181967 A1 | 7/2008 | Liu et al. | |
| 2008/0233552 A1 | 9/2008 | Ma et al. | |
| 2009/0012629 A1 | 1/2009 | Yao et al. | |
| 2009/0036996 A1 | 2/2009 | Roeber | |
| 2009/0142831 A1 | 6/2009 | Hariri | |
| 2009/0291891 A1 | 11/2009 | Neufeld | |
| 2010/0028849 A1 | 2/2010 | Shelby et al. | |
| 2010/0104539 A1 * | 4/2010 | Daniel | A61L 27/3604 424/93.7 |

(Continued)

FOREIGN PATENT DOCUMENTS

| | | |
|---|---|---|
| CN | 101433556 | 5/2009 |
| CN | 102272289 A | 12/2011 |

(Continued)

OTHER PUBLICATIONS

International Search Report and Written Opinion for PCT/US2013/054322, mailed Oct. 22, 2013.
U.S. Appl. No. 13/719,148, filed Feb. 13, 2012, Morse et al.
U.S. Appl. No. 13/744,331, filed Jan. 17, 2013, Koob et al.
U.S. Appl. No. 13/745,642, filed Jan. 18, 2013, Koob et al.
U.S. Appl. No. 13/787,612, filed Mar. 6, 2013, Morse et al.
U.S. Appl. No. 13/815,747, filed Mar. 15, 2013, Daniel et al.
U.S. Appl. No. 13/815,784, filed Mar. 15, 2013, Koob et al.
U.S. Appl. No. 13/815,873, filed Mar. 15, 2013, Brown et al.
U.S. Appl. No. 13/983,301, filed Feb. 13, 2012, Morse et al.
U.S. Appl. No. 13/967,326, filed Aug. 14, 2013, Koob et al.
U.S. Appl. No. 13/963,984, filed Aug. 9, 2013, Daniel et al.

(Continued)

Primary Examiner — Robert S Cabral
(74) Attorney, Agent, or Firm — Alston & Bird LLP (57) ABSTRACT Described herein are compositions composed of micronized particles derived from one or more components present in placental tissue in combination with one or more bone grafts. The compositions have numerous medical applications. Methods for making and using the micronized compositions are also described herein.

15 Claims, 3 Drawing Sheets

(56) References Cited

U.S. PATENT DOCUMENTS

| | | |
|---|---|---|
| 2010/0136114 A1 | 6/2010 | Mao |
| 2010/0143312 A1 | 6/2010 | Hariri et al. |
| 2010/0178297 A1 | 7/2010 | Carmeliet et al. |
| 2010/0209408 A1* | 8/2010 | Stephen A et al. ........ 424/93.71 |
| 2010/0260847 A1 | 10/2010 | Hariri |
| 2010/0272782 A1 | 10/2010 | Owens et al. |
| 2011/0044997 A1 | 2/2011 | Rankin et al. |
| 2011/0177150 A1 | 7/2011 | Pathak et al. |
| 2011/0189301 A1 | 8/2011 | Yang et al. |
| 2011/0206776 A1 | 8/2011 | Tom et al. |
| 2011/0307059 A1 | 12/2011 | Young et al. |
| 2012/0010708 A1 | 1/2012 | Young et al. |
| 2012/0030963 A1 | 2/2012 | Durance et al. |
| 2012/0078378 A1 | 3/2012 | Daniel et al. |
| 2013/0230561 A1 | 9/2013 | Daniel et al. |
| 2014/0255508 A1 | 9/2014 | Morse et al. |
| 2014/0302162 A1 | 10/2014 | Morse et al. |
| 2014/0342014 A1* | 11/2014 | Tseng ..................... A61K 35/50 424/572 |

FOREIGN PATENT DOCUMENTS

| | | |
|---|---|---|
| EP | 0 431 164 | 6/1991 |
| EP | 0431479 A1 | 6/1991 |
| JP | 2007-106760 | 4/2007 |
| KR | 10/1991/0011272 | 8/1991 |
| KR | 10/1991/0011727 | 8/1991 |
| KR | 2001/100588 | 11/2001 |
| KR | 10-2006-0057850 | 5/2006 |
| WO | WO-01/08716 A1 | 2/2001 |
| WO | WO-2004/026244 | 4/2004 |
| WO | WO-2005/017165 | 2/2005 |
| WO | WO-2009/033160 | 3/2009 |
| WO | WO-2009/048908 | 4/2009 |
| WO | WO-2009/132186 A1 | 10/2009 |
| WO | WO-2010/029344 | 3/2010 |
| WO | WO-2010/051032 A1 | 5/2010 |
| WO | WO-2012/003377 | 1/2012 |
| WO | WO-2012/112410 | 8/2012 |
| WO | WO-2012/112417 A2 | 8/2012 |
| WO | WO-2012/112441 A1 | 8/2012 |

OTHER PUBLICATIONS

U.S. Appl. No. 14/050,218, filed Oct. 9, 2013, Brown et al.
"MiMedx Group Announces Launch of EpiFixTM and Hiring of Vice President, Wound Care," Mimedx Press Release (2011).
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
EpiFix Produce Brochure (2011).
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Mayfield et al., "Watertight closure of spinal dura mater: Technical note," J. Neurosurg., (1975), 43(5):639-640.
U.S. Appl. No. 13/815,753, filed Mar. 15, 2013, Koob et al.
U.S. Appl. No. 13/688,091, filed Nov. 28, 2012, Spencer et al.
U.S. Appl. No. 13/744,332, filed Jan. 17, 2013, Pringle et al.
PCT International Preliminary Report on Patentability for copending PCT Application No. PCT/US2012/024798, dated Feb. 1, 2013.
PCT International Search Report and Written Opinion for copending PCT Application No. PCT/US2013/054319, dated Nov. 13, 2013.
PCT International Search Report and Written Opinion for copending PCT Application No. PCT/US2013/055003, dated Nov. 19, 2013.
PCT International Search Report and Written Opinion for copending PCT Application No. PCT/US2013/054320, dated Nov. 6, 2013.
PCT International Search Report and Written Opinion for copending PCT Application No. PCT/US2012/66862, dated Feb. 12, 2013.
PCT International Search Report and Written Opinion for copending PCT Application No. PCT/US2013/054325, dated Oct. 28, 2013.
PCT International Search Report for copending PCT Application No. PCT/US2012/024798, dated Jun. 20, 2012.
Tao, et al., "Implantation of amniotic membrane to reduce postlaminectomy epidurla adhesions," Eur. Spine. J., (2009), 18:1202-1212.
MiMedx Press Release, "MiMedx Scientific Study is Electronically Published in the International Wound Journal", 2013.
Nagaya et al., "Transplantation of mesenchymal stem cells improves cardiac function in a rat model of dilated cardiomyopathy", Circulation, 2005, 112(8):1128-1135.
Parolini et al., "Toward cell therapy using placenta-derived cells: disease mechanisms, cell biology, preclinical studies, and regulatory aspects at the round table", Stem Cells and Development, 2010, 19(2):143-154.
PCT International Preliminary Report on Patentability dated Jan. 16, 2014 in PCT Patent Application No. PCT/US12/66862.
PCT International Search Report and Written Opinion for PCT/US2014/012141, dated May 20, 2014.
AzoMaterials. Particle Size—US Sieve Series and Tyler Mesh Size Equivalents. Datasheet [online]. AZoM.com, Copyright 2000-2015. Updated Jun. 11, 2013 [retrieved on Sep. 24, 2015]. Retrieved from the Internert: URL:http://www.azom.com/article.aspx?ArticleID=1417.
Mardovin et al., "The "Super" Expansion Graft", J Burn Care Rehabil, Sep./Oct. 1992, pp. 556-559 vol. 13, No. 5, pp. 556-559.
Rasenack, N. et al., "Micron-size drug particles: common and novel micronization techniques", Pharmaceutical Development and Technology, 2004, 9(1): 1-13.
Stedman's Online Dictionary. Bursa. Datasheet [online]. Lippincott Williams & Wilkins Copyright 2009 [retrieved on Sep. 24, 2015]. Retrieved from the internet: <URL: http://www.azom.com/article.aspx?ArticleD=1417>pg.2.
Uchide et al., "Possible Roles of Proinflammatory and Chemoattractive Cytokines Produced by Human Fetal Membrane Cells in the Pathology of Adverse Pregnancy Outcomes Associated with Influenza Virus Infection", Mediators of Inflammation, 2012, vol. 2012; Article ID 270670, 32 pages.
Database WPI XP002732611 & KR 2001-0100588, dated Nov. 14, 2001—Abstract.
Derwent Abstract for KR 200110588, original document published Nov. 2001.
Extended European Search Report dated Dec. 2, 2014, for European Patent Application No. EP 12746721.
http://proxybiomedical.com/Images/ML005-01-Rev002.pdf (accessed on Jun. 5, 2014.).
International Preliminary Report on Patentability dated Dec. 8, 2014, for International Patent Application No. PCT/US2013/054322.
International Preliminary Report on Patentability dated Dec. 8, 2014, for International Patent Application No. PCT/US2013/054325.
International Preliminary Report on Patentability dated Nov. 28, 2014, for International Patent Application No. PCT/US2013/054319.
International Preliminary Report on Patentability dated Nov. 27, 2014, for International Patent Application No. PCT/US2013/055003.
International Preliminary Report of Patentability dated Sep. 25, 2014, for International Patent Application PCT/US2013/064146.
International Search Report and Written Opinion dated Aug. 12, 2014 for International Patent Application No. PCT/US13/63736.
Office Action for European Application No. 13844862.6 dated Nov. 16, 2018, 4 pages.

(56) References Cited

OTHER PUBLICATIONS

Office Action for Japanese Application No. 2018-128094 dated May 28, 2019.
Koob et al., "Biological properties of dehydrated human amnion-chorion composite graft: implications for chronic wound healing", International Wound Healing, 2013, 10(5):493-500.
PCT International Search Report and Written Opinion dated Jan. 9, 2014 in related PCT Patent Application No. PCT/US2013/064146.

* cited by examiner

MICRONIZED COMPOSITIONS COMPOSED OF BONE GRAFTS AND METHODS OF MAKING AND USING THE SAME

CROSS REFERENCE TO RELATED APPLICATIONS

This application claims priority upon U.S. provisional application Ser. No. 61/543,934, filed Oct. 6, 2011. This application is hereby incorporated by reference in its entirety.

BACKGROUND OF THE INVENTION

1. Field of the Invention

This invention is directed to bone grafts comprising micronized placental tissue including micronized amnion and/or chorion. The inclusion of such micronized tissue in bone grafts provides for a number of medical applications including methods for enhancing the therapeutic outcome of such bone graft transplantations.

2. State of the Art

Described herein are compositions composed of micronized particles derived from one or more components present in placental tissue in combination with one or more bone grafts. The compositions have numerous medical applications. Methods for making and using the micronized compositions are also described herein.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

SUMMARY OF THE INVENTION

The present disclosure provides a micronized composition comprising micronized particles derived from one or more placental components, and one or more bone grafts. In various embodiments, the placental components comprise amniotic membrane, amnion, chorion, Wharton's jelly, placental disk, or any combination thereof.

In one aspect, the micronized particles have a particle size less than 1,000 µm. In another aspect, the micronized particles have a particle size from 200 µm to 300 µm. In other aspects, the micronized particles are 100% micronized amnion. In yet another aspect, the micronized particles are 100% micronized chorion.

In other embodiments, the micronized particles are micronized amnion and/or chorion with Wharton's jelly. In further embodiments, the bone graft is an autograft, an allograft, a xenograft, an alloplast, or any combination thereof. In one embodiment, the amount of micronized particles to bone graft is from 1:99 to 99:1 by volume.

Other exemplary embodiments provide a micronized composition as described further comprising a pharmaceutically-acceptable carrier. In certain aspects, the pharmaceutically acceptable carrier comprises water, saline, Ringer's solution, dextrose solution, Hank's solution, a buffer, or a nonaqueous vehicle. In some aspects, the buffer comprises a phosphate buffer, bicarbonate buffer, or Tris buffer. In additional embodiments, the pharmaceutically acceptable carrier comprises a biocompatible filler. In certain aspects, the filler is carboxymethylcellulose, cellulose, hyaluronic acid or a salt thereof, glycerin, or any combination thereof. In various embodiments of the invention, the micronized composition is injectable. In other aspects, the composition is a foam, gel, or putty, or paste.

In yet another embodiment, the invention provides a composition produced by the process comprising (a) micronizing one or more placental components to produce micronized particles; and (b) admixing the micronized particles with one or more bone grafts. In some aspects, step (a) is performed by mechanical grinding or shredding. In other aspects, step (a) is performed by cryogenic grinding.

The micronized composition of the invention can be used in a spinal application. In other aspects, the micronized composition can be used in a method for treating or preventing inflammation in a joint of a subject, the method comprising injecting the micronized composition into the joint.

Other embodiments of the invention include a method for fusing two or more bones together, the method comprising (1) applying the micronized composition to one or more of the bones and (2) contacting the bones with each other via the composition. In another embodiment, the invention provides a method for filling a bone void, the method comprising injecting the micronized composition into the void. In yet another embodiment, the invention provides a method for treating or preventing inflammation in a joint of a subject, the method comprising injecting a micronized composition comprising micronized particles derived from one or more placental components into the joint. In a further embodiment, a method for fusing two or more bones together is provided, the method comprising (1) applying a micronized composition comprising micronized particles derived from one or more placental components to one or more of the bones and (2) contacting the bones with each other via the composition. In yet another embodiment, a method for filling a bone void is provided, the method comprising injecting a micronized composition comprising micronized particles derived from one or more placental components into the void.

The invention, in further exemplary embodiments, provides a three-dimensional construct comprising (a) micronized amnion and intermediate tissue layer, wherein the micronized amnion and intermediate tissue layer are treated with a cross-linking agent, and optionally (b) one or more bone grafts. In one aspect, the three-dimensional construct comprises (a) micronized amnion membrane and chorion, wherein the micronized amnion membrane and chorion are treated with a cross-linking agent, and optionally (b) one or more bone grafts. In certain aspects, the construct may be used in orthopedic or spinal applications. In other aspects, the application is for void filling or for structural support. In further aspects, the construct may be used as a socket filler after tooth extraction.

In another embodiment, the invention provides a micronized composition suitable for use in treating a bone defect, which composition comprises (a) micronized particles derived from one or more placental components; (b) one or more bone grafts; (c) a pharmaceutically acceptable carrier; and (d) a biodegradable filler. In one aspect of the embodiment, it shall be understood that the composition comprises only those components that do not materially alter the basic characteristics of the composition. In another aspect of the embodiment, the composition comprises only the components specifically recited therein.

BRIEF DESCRIPTION OF THE DRAWINGS

The accompanying drawings, which are incorporated in and constitute a part of this specification, illustrate several aspects described below.

DETAILED DESCRIPTION

Before the present articles and methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" as used herein is any vertebrate organism.

The term "amnion membrane" as used herein includes amniotic tissue where the intermediate tissue layer has not been removed.

The term "amnion" as used herein includes amnion tissue where the intermediate tissue layer has been removed.

The term "admixing" as used herein is defined as mixing the two components together so that there is no chemical reaction or physical interaction. The term "admixing" also includes the chemical reaction or physical interaction between the compound and the pharmaceutically-acceptable compound.

The term "placental tissue" as used herein includes any components, such as any materials or tissues present in the placenta and the umbilical cord which have been washed and decontaminated. In one aspect, placental components include, but are not limited to, amniotic membrane, amnion, chorion, Wharton's jelly, or any combination thereof. As such, "placental tissue" and "placental components" are used interchangeably herein.

The term "micronized placental tissue" as used herein includes placental tissue as defined above which has been subjected to micronization using any techniques known in the art, including but not limited to, mechanical grinding or shredding, cryogenic grinding, milling, ball milling, wet milling, high pressure homogenization, emulsification and precipitation, precipitation with a compressed fluid antisolvent, spray freezing into a liquid, rapid expansion from a liquefied-gas solution, evaporative precipitation into an aqueous solution and air jet micronization.

The term "bone defect" as used herein refers to any bone deficient region, such as a void, gap, recess or other discontinuity in the bone. The bone defect can be artificially or naturally established and can occur due to disease or trauma, for example. Thus, the bone defect can occur as a consequence of pathologic, inflammatory, or tumor diseases, surgical interventions, congenital defects, or bone fractures, and the like. For example, in the case of certain diseases, such as bone tumors, the bone defect is artificially established by removing the tumor tissue. Thus, according to the method of the subject invention, the composite can be applied, for example, to repair periodontal defects, for craniofacial reconstruction, joint reconstruction, fracture repair, to conduct orthopedic surgical procedures, and spinal fusion, for example.

Titles or subtitles may be used in the specification for the convenience of a reader, which are not intended to influence the scope of the present invention. Additionally, some terms used in this specification are more specifically defined below.

I. Micronized Particles and Methods for Making Thereof

Described herein are compositions composed of micronized placental tissue and pharmaceutical compositions thereof. Compositions comprising micronized placental tissue are described in PCT Application No. PCT/US12/24798, as well as in U.S. provisional application Ser. Nos. 61/442, 346 and 61/543,995. The contents of these applications are specifically incorporated by reference in their entireties.

Described herein are micronized compositions composed of (a) micronized particles derived from one or more placental components, and (b) one or more bone grafts.

Figure 1:
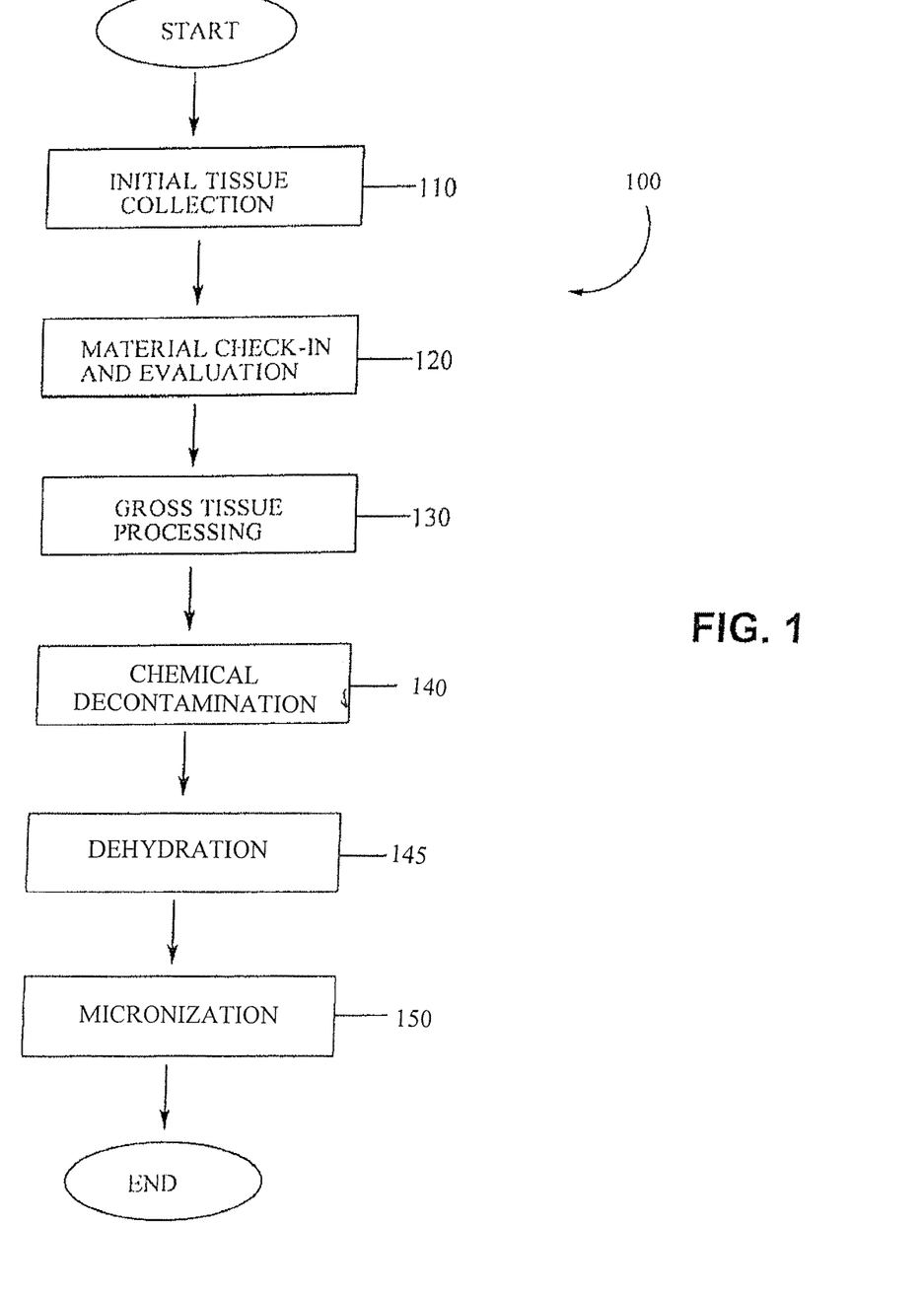
FIG. 1 is an overview flow chart of the process for making the micronized compositions described herein.

FIG. 1 depicts an overview (100) and certain aspects of the steps to harvest, process, and prepare placental material for use in the preparation of the micronized compositions described herein. More detailed descriptions and discussion regarding each individual step will follow. Initially, the placental tissue is collected (step 110). The material is preserved and transported in conventional tissue preservation manner to a suitable processing location or facility for check-in and evaluation (step 120). Gross processing, handling, and separation of the tissue layers then takes place (step 130). Acceptable tissue is then decontaminated (step 140). After decontamination, the placental components (e.g., amnion membrane, amnion, chorion, Wharton's jelly, placental disk) are dehydrated (step 145) and subsequently micronized to produce micronized particles (step 150). Finally, the micronized particles are mixed with one or more bone grafts to produce micronized compositions (step 160). Each step is described in detail below.

Initial Tissue Collection (Step 110)

The components used to produce the micronized particles are derived from placental tissue. The source of the placental tissue can vary. In one aspect, placental tissue produced from a mammal such as human and other animals including, but not limited to, cows, pigs, and the like can be used herein. In the case of humans, the recovery of placental tissue originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), hepatitis B surface antigens (HBsAg), antibodies to the hepatitis C virus (anti-HCV), antibodies to the human T-lymphotropic virus type I and type II (anti-HTLV-I and anti-HTLV-II), CMV, and syphilis, using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta tissue is collected prior to the completion or obtaining of results from the screening tests and delivery cultures, such tissue is labeled and kept in quarantine. The tissue is approved for further processing only after the required screening assessments and delivery cultures, which declare the tissue safe for handling and use, are satisfied and obtains final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue further are assembled in a staging area in a controlled environment and are prepared for introduction into a controlled environment. If the controlled environment is a manufacturing hood, the sterile supplies are opened and placed into the hood using conventional sterile technique. If the controlled environment is a clean room, the sterile supplies are opened and placed on a cart covered by a sterile drape. All the work surfaces are covered by a piece of sterile drape using conventional sterile techniques, and the sterile supplies and the processing equipments are placed on to the sterile drape, again using conventional sterile techniques.

Processing equipment is decontaminated according to conventional and industry-approved decontamination procedures and then introduced into the controlled environment. The equipment is strategically placed within the controlled environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains hyperisotonic saline solution (e.g., 18% NaCl) that is at room or near room temperature. The placenta is gently massaged to help separate blood clots and to allow the placental tissue to reach room temperature, which will make the separation of the amnion and chorion membranes from each other, as discussed hereinafter, easier. After having warmed up to the ambient temperature (after about 10-30 minutes), the placenta is then removed from the sterile processing basin and laid flat on a processing tray with the amnion membrane layer facing down for inspection.

The placenta tissue is examined for discoloration, debris or other contamination, odor, and signs of damage. The size of the tissue is also noted. A determination is made, at this point, as to whether the tissue is acceptable for further processing.

Next, if the placenta tissue is deemed acceptable for further processing, the amnion membrane and chorion membrane of the placenta tissue are then carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion membrane can be separated from the chorion membrane. The amnion membrane appears as a thin, opaque layer on the chorion.

The fibroblast layer is identified by gently contacting each side of the amnion membrane with a piece of sterile gauze or a cotton tipped applicator. The fibroblast layer will stick to the test material. The amnion membrane is placed into processing tray basement membrane layer down. Using a blunt instrument, a cell scraper or sterile gauze, any residual blood is also removed. This step must be done with adequate care, again, so as not to tear the amnion membrane. The cleaning of the amnion membrane is complete once the amnion membrane is smooth and opaque-white in appearance. If the amnion membrane is cleaned too much, the jelly-like fibroblast layer can be removed. Any areas of the amnion membrane cleaned too aggressively and appearing clear will be unacceptable and will ultimately be discarded.

The removal of epithelial cells from the amnion is optional. In an embodiment, the epithelial cell layer of the amnion is not removed. In an embodiment, the epithelium layer present on the amnion is substantially removed in order to expose the basement layer of the amnion. The term "substantially removed" with respect to the amount of epithelium removed is defined herein as removing greater than 90%, greater than 95%, or greater than 99% of the epithelial cells from the amnion.

In certain aspects, the intermediate tissue layer is removed from the amnion membrane. This can be performed by peeling the intermediate tissue layer from the amnion membrane. Alternatively, the intermediate tissue layer can be removed from the amnion membrane by wiping the intermediate tissue layer with a gauze or other suitable wipe. The resulting amnion can be subsequently decontaminated using the process described below. The intermediate tissue layer does not require any additional processing and can be used as-is.

In certain aspects, the Wharton's jelly can optionally be isolated using the following procedure. Using a scalpel or scissors, the umbilical cord is dissected away from the chorionic disk. Once the veins and the artery have been identified, the cord is dissected lengthwise down one of the veins or the artery. Once the umbilical cord has been dissected, surgical scissors and forceps can be used to dissect the vein and artery walls from the Wharton's jelly. Next, the outer layer of amnion is removed from the Wharton's jelly by cutting the amnion. After removing the amnion from the Wharton's jelly, the Wharton's jelly can be cut into strips. In one aspect, the strips are approximately 1-4 cm by 10-30 cm with an approximate thickness of 1.25 cm; however, other thicknesses are possible depending on application.

Chemical Decontamination (Step 140)

In one aspect, the amnion produced in step 130 is then placed into a sterile Nalgene jar for the next step for additional cleaning In one aspect, the following procedure can be used to clean the amnion. Each Nalgene jar is aseptically filled with 18% saline hypertonic solution and sealed (or sealed with a top). The jar is then placed on a rocker platform and agitated for between 30 and 90 minutes, which further cleans the tissue of contaminants. If the rocker platform was not in the critical environment (e.g., the manufacturing hood), the Nalgene jar is returned to the controlled/sterile environment and opened. Using sterile forceps or by aseptically decanting the contents, the tissue is gently removed from the Nalgene jar containing the 18% hyperisotonic saline solution and placed into an empty Nalgene jar. This empty Nalgene jar with the tissue is then aseptically filled with a pre-mixed antibiotic solution. Preferably, the premixed antibiotic solution is comprised of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the tissue. This jar or container containing the tissue and antibiotics is then sealed or closed and placed on a rocker platform and agitated for, preferably, between 60 and 90 minutes. Such rocking or agitation of the tissue within the antibiotic solution further cleans the tissue of contaminants and bacteria. Optionally, the amnion can be placed into 200 ml of 0.5% Triton-X wash solution.

Again, if the rocker platform was not in the critical environment (e.g., the manufacturing hood), the jar or container containing the tissue and antibiotics is then returned to the critical/sterile environment and opened. Using sterile forceps, the tissue is gently removed from the jar or container and placed in a sterile basin containing sterile water or normal saline (0.9% saline solution). The tissue is allowed to soak in place in the sterile water/normal saline solution for at least 10 to 15 minutes. The tissue may be slightly agitated to facilitate removal of the antibiotic solution and any other contaminants from the tissue. After at least 10 to 15 minutes, the tissue is ready to be dehydrated and processed further.

In another aspect, the amnion membrane can be decontaminated using the process described above followed by the removal of the intermediate tissue layer.

In the case when the chorion is to be used, the following exemplary procedure can be used. After separation of the chorion from the amnion and removal of clotted blood from the fibrous layer, the chorion is rinsed in 18% saline solution for 30 min. During the first rinse cycle, 18% saline is heated in a sterile container using laboratory heating plate such that the solution temperature is approximately 48° C. The solution is decanted, the chorion tissue is placed into the sterile container, and decanted saline solution is poured into the container. The container is sealed and placed on rocker plate and agitated for 1 hour. After 1 hour agitation bath, remove the tissue and place the tissue into second heated agitation bath for an additional 1 hour rinse cycle. Optionally, the chorion tissue can be placed into 200 ml of 0.5% Triton-X wash solution. The container is sealed and agitated without heat for 2 hours. The tissue is next washed with deionized water (250 ml of DI water×4) with vigorous motion for each rinse. The tissue is removed and placed into a container of 1× PBS w/EDTA solution. The container is sealed and agitated for 1 hour at controlled temperature for 8 hours. The tissue is removed and rinsed using sterile water. A visual inspection was performed to remove any remaining discolored fibrous blood material from the membrane. The membrane should have a cream white visual appearance with no evidence of brownish discoloration. After decontamination, the chorion is dehydrated prior to micronization.

In the case of Wharton's jelly, it can be transferred to a sterile Nalgene jar. Next, room temperature 18% hypertonic saline solution is added to rinse the tissue and the jar is sealed. The jar is agitated for 30 to 60 minutes. After incubation, the jar is decontaminated and returned to the sterile field. The tissue is transferred to a clean sterile Nalgene jar and prewarmed (about 48° C.) 18% NaCl is added. The container is sealed and placed on rocker plate and agitated for 60 to 90 minutes.

In one aspect, after the rinse, the jar is decontaminated and returned to the sterile field. The tissue is removed and placed into an antibiotic solution. The container is sealed and agitated for 60 to 90 minutes on a rocker platform. Following incubation, the jar may be refrigerated at 1 to 10° C. for up to 24 hours. The Wharton's jelly is next transferred to a sterile basin containing approximately 200 mL of sterile water. The tissue is rinsed for 1-2 minutes and transferred to a sterile Nalgene jar containing approximately 300 ml of sterile water. The jar is sealed and placed on the rocker for 30 to 60 minutes. After the incubation, the jar is returned to the sterile field. The Wharton's jelly should have a cream white visual appearance with no evidence of brownish discoloration. The tissue is ready for further processing.

Dehydration (Step 145)

In one aspect, the placental components (e.g., amnion membrane or amnion, intermediate tissue layer, chorion, Wharton's jelly, placental disk) are processed into tissue grafts that are subsequently micronized. In one aspect, the placental component is laid on a suitable drying fixture. The drying fixture is preferably sized to be large enough to receive the placental component, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Georgia. Any other suitable material that is heat and cut resistant, capable of being formed into an appropriate shape to receive wet tissue can also be used for the drying fixture.

In another embodiment, a drying chamber or dehydration device can be used in a suitable manner as described in U.S. provisional application Ser. Nos. 61/683,700, 61/683,699, 61/683,698 and 61/683,697. The contents of these applications are specifically incorporated by reference in their entireties.

Once the placental component is placed on the drying fixture, the drying fixture is placed in a sterile Tyvex (or similar, breathable, heat-resistant, and sealable material) dehydration bag and sealed. Such breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed. The Tyvex dehydration bag containing the one or more drying fixtures is then placed into a non-vacuum oven or incubator that has been preheated to approximately 35 to 50 degrees Celcius. The Tyvex bag remains in the oven for between 30 and 120 minutes, although approximately 45 minutes at a temperature of approximately 45 degrees Celcius appears to be ideal to dry the tissue sufficiently but without over-drying or burning the tissue. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

Preparation of Micronized Compositions (Step 150)

Once the placental components (e.g., amnion membrane or amnion, intermediate tissue layer, chorion, Wharton's jelly, placental disk) have been isolated, decontaminated and dehydrated, the placental components are micronized to produce micronized particles. The selection of placental components used to make the micronized particles can vary depending upon the application and the selection of bone grafts. In one aspect, the micronized particles are composed of 100% amnion, chorion, or Wharton's jelly. In another aspect, the micronized particles are composed of a mixture of amnion and chorion, where the amount of amnion to chorion can be from 1:99 to 99:1, 20:80 to 80:20, 40:60 to 60:40, or about 50:50 by wt %. In another aspect, the micronized particles are composed of a mixture of chorion and Wharton's jelly, where the amount of chorion to Wharton's jelly can be from 1:99 to 99:1, 20:80 to 80:20, 40:60 to 60:40, or about 50:50 by wt %. In a further aspect, the micronized particles are composed of a mixture of amnion, chorion, and Wharton's jelly, where the amount of amnion is from 10% to 50%, or 20% to 40% by weight, the amount of chorion is from 20% to 60%, or 30% to 50% by weight, and the amount of Wharton's jelly is from 20% to 60%, or 30% to 50% by weight of the micronized particles.

The micronized compositions can be produced using instruments known in the art. For example, the Retsch Oscillating Mill MM400 can be used to produce the micronized compositions described herein. The particle size of the materials in the micronized composition can vary as well depending upon the application of the micronized composition. In one aspect, the micronized composition has particles that are less than 1,000 µm, less than 500 µm, from 25 µm to 500 µm, from 25 µm to 300 µm, from 25 µm to 200 µm. In another aspect, the micronized composition has particles that are from 100 µm to 300 µm, or from 200 µm to 300 µm. In one aspect, the micronized composition has particles that have a diameter less than 150 µm, less than 100 µm, or less than 50 µm. In other aspects, particles having a larger diameter (e.g. 150 µm to 350 µm) are desirable. In all cases, the diameter of the particle is measured along its longest axis.

In one embodiment, the size of the particles may be reduced to nano-range. As one skilled in the art would understand, nanoparticles of placental components may be desirable for the increased density and/or increased release rate upon applying to the wound. Preferably, the particle size of the micronized particles is from about 0.05 µm to about 2 µm, from about 0.1 µm to about 1.0 µm, from about 0.2 µm to about 0.8 µm, from about 0.3 µm to about 0.7 µm, or from about 0.4 µm to about 0.6 µm. Alternatively, the particle size of the micronized particles is at least 0.05 µm, at least 0.1 µm, at least 0.2 µm, at least 0.3 µm, at least 0.4 µm, at least 0.5 µm, at least 0.6 µm, at least 0.7 µm, at least 0.8 µm, at least 0.9 µm, or at least 1 µm. Alternatively, the particle size of the micronized particles is less than 1 µm, less than 0.9 µm, less than 0.8 µm, less than 0.7 µm, less than 0.6 µm, less than 0.5 µm, less than 0.4 µm, less than 0.3 µm, less than 0.2 µm, less than 0.1 µm, or less than 0.05 µm.

In other aspects, particles having a range of sizes and volumes are preferred as such particles will impart differential release rates into the wound. In one embodiment, particles having a range of mass to volume ratios can be prepared by either micronizing a mixture of a monolayer graft with multi-layer grafts (e.g., 2-10 layers) such that a range of graft sizes and volumes are provided. In another embodiment, particles of varying surface area to volume ratios of the same tissue material can be prepared by compressing the linear grafts into three-dimensional shapes of varying sizes (round, elliptical, oblong, etc.). As surface area to volume ratio is increased, particle dissipation increases due to the larger exposure area for endogenous enzymes, etc. This results in a faster rate of release of collagen types IV, V, and VII, cell-adhesion bio-active factors including fibronectin and laminins and other components of the micronized particles. On the other hand, as the surface area to volume ratio is decreased, particle dissipation decreases due to the smaller exposure area for endogenous enzymes, etc. This results in a slower rate of release of collagen types IV, V, and VII, cell-adhesion bio-active factors including fibronectin and laminins and other components of the micronized particles. In combination, the use of a layer of micronized particles having different surface area to volume ratios provides for a "time-release" mechanism whereby the benefits of the micronized graft are both immediate and prolonged.

In one embodiment, the surface area to volume ratio (based on a sphere having a range of diameters as described above) is between the range of about 0.06 µm to about $6\times10^4$ µm, about 0.06 µm to about $6\times10^3$ µm, about 0.06 µm to about $6\times10^2$ µm, or about 0.6 µm to about $6\times10^2$ µm.

In one aspect, micronization is performed by mechanical grinding or shredding. In another aspect, micronization is performed by cryogenic grinding. In this aspect, the grinding jar containing the placental components is continually cooled with liquid nitrogen from the integrated cooling system before and during the grinding process. Thus the sample is embrittled and volatile components are preserved. Moreover, the denaturing of proteins in the amnion or amnion membrane, intermediate tissue layer, and chorion is minimized or prevented. In one aspect, the CryoMill manufactured by Retsch can be used in this aspect.

In another aspect, a bioactive agent can be added to the composition of placental components prior to and/or after micronization. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the micronized composition with bioactive agent to the region of interest, the bioactive agent is delivered to the region over time.

In one aspect, the amnion membrane or amnion can be cross-linked with the intermediate tissue layer or chorion. For example, a cross-linking agent can be added to the composition prior to and/or after micronization. In general, the cross-linking agent is nontoxic and non-immunogenic. When the amnion membrane or amnion, intermediate tissue layer, and chorion are treated with the cross-linking agent, the cross-linking agent can be the same or different. In one aspect, the amnion membrane or amnion, intermediate tissue layer, and chorion can be treated separately with a cross-linking agent or, in the alternative, the amnion membrane or amnion, intermediate tissue layer, and chorion can be treated together with the same cross-linking agent. In certain aspects, the amnion membrane or amnion, intermediate tissue layer, and chorion can be treated with two or more different cross-linking agents. The conditions for treating the amnion membrane or amnion, intermediate tissue layer, and chorion can vary. In other aspects, the amnion membrane or amnion, intermediate tissue layer, and/or chorion can be micronized and the micronized composition can subsequently be treated with a cross-linking agent. In one aspect, the concentration of the cross-linking agent is from 0.1 M to 5 M, 0.1 M to 4 M, 0.1 M to 3 M, 0.1 M to 2 M, or 0.1 M to 1 M.

The cross-linking agent generally possesses two or more functional groups capable of reacting with proteins to produce covalent bonds. In one aspect, the cross-linking agent possesses groups that can react with amino groups on proteins present in the amnion, intermediate tissue layer, and chorion. Examples of such functional groups include, but are not limited to, hydroxyl groups, substituted or unsubstituted amino groups, carboxyl groups, and aldehyde groups. In one aspect, the cross-linker can be a dialdehydes such as, for example, glutaraldehyde. In another aspect, the cross-linker can be a carbodiimide.

In one aspect, sugar is the cross-linking agent, where the sugar can react with proteins present in the amnion, intermediate tissue layer, and chorion to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as cross-linking agent include, but are not limited to, D-ribose, glycerone, altrose, talose, ertheose, glucose, lyxose, mannose, xylose, gulose, arabinose, idose, allose, galactose, maltose, lactose, sucrose, cellibiose, gentiobiose, melibiose, turanose, trehalose, isomaltose, or any combination thereof.

Preparation of Micronized Compositions with Bone Grafts (Step 160)

Once the micronized particles are produced, they can be admixed with one or more bone grafts. Bone grafts are a tissue or material used to repair a defect or deficiency in osseous tissue. Bone grafts generally fall into four categories: autografts, which are obtained from the patient, and allografts, xenografts and alloplasts. Bone grafts generally possess one or more of the following characteristics: (1) ostegenic potential-the presence of viable cells; (2) osteoinductive-contains noncollagenous proteins that attract cells, induce bone formation, and or hasten cell migration; and (3) osteoconductive-serves as scaffold for cellular migration and provides calcium phosphate.

Autograft bone harvested from the iliac crest, rib, chin, or intraoral cancellous bone from the maxillary tuberosity or extraction sites, possesses osteogenic, osteoinductive, and osteoconductive properties. Allograft materials refer to tissue derived from human cadavers, and include iliac cancellous bone and marrow, freeze-dried cortical and cancellous bone, and demineralized freeze-dried cortical and cancellous bone. Caderivic allografts possess osteoconductive and osteoinductive properties. Xenografts are derived from non-human species. These graft materials only possess osteoconductive properties as all or most of the proteinaceous material is removed leaving behind an inert absorbable hydroxapapatite scaffolding. Alloplasts are synthetically manufactured and include non-porous hydroxyapatite, porous hydroxyapatite, tri-calcium phosphate, bioactive glass, fluoroapatite, carbonated apatite, calcium sulfate, calcium carbonate, and combinations thereof, and provide varying degrees of osteoconductive properties.

The micronized particles and bone grafts can be admixed with one another using techniques known in the art. The micronized particles and bone grafts can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, cellulose, hyaluronic acid or a salt thereof, glycerin, sorbitol, dextran, or any combination thereof. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. Additionally, the pharmaceutical compositions can include carriers, thickeners, diluents, preservatives, surface active agents and the like in addition to the compounds described herein.

The pharmaceutical compositions can be prepared using techniques known in the art. In one aspect, the composition is prepared by admixing the micronized particles and bone graft(s) with a pharmaceutically-acceptable compound and/or carrier.

It will be appreciated that the actual preferred amounts of micronized particles and bone graft in a specified case will vary according to the specific compound being utilized, the particular compositions formulated, the mode of application, and the particular situs and subject being treated. In one aspect, the amount of micronized particles to bone graft is from 1:99 to 99:1, 1:50 to 50:1, 1:10 to 10:1, 2:8 to 8:2, 4:6 to 6:4, or about 1:1 by volume Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999).

The pharmaceutical compositions described herein can be administered in a number of ways depending on whether local or systemic treatment is desired, and on the area to be treated. In one aspect, administration can be by injection, where the micronized composition is formulated into a liquid, gel, putty, paste, or sponge (i.e., freeze dried). In other aspects, the micronized composition can be formulated to be applied internally to a subject. In other aspects, the micronized composition can be applied topically (including ophthalmically, vaginally, rectally, intranasally, orally, or directly to the skin). Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

In certain aspects, the micronized composition can be used to form a three-dimensional construct. For example, the micronized particles with the bone graft can be treated with a cross-linking agent described above then placed in a mold having specific dimensions. Alternatively, the micronized particles with the bone graft can be placed into the mold and subsequently treated with the cross-linking agent. In other aspects, the cross-linked particles can be manually formed into any desired shape. Not wishing to be bound by theory, the three-dimensional construct composed of smaller micronized particles will produce a denser product capable of bearing mechanical loads. Alternatively, larger micronized particles will produce constructs that are less dense and possess compressive properties. This feature can be useful in non-load void filling, especially where it is desirable to have a product that will conform to irregular shapes. The three-dimensional constructs can include one or more bioactive agents described herein.

II. Applications of Micronized Compositions

Figure 2:
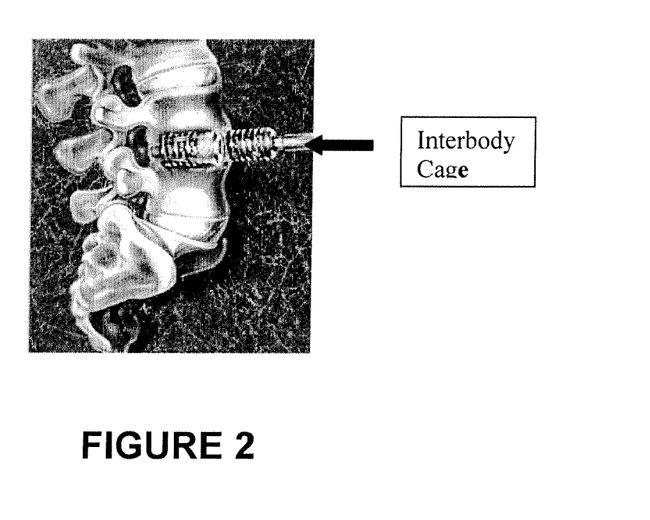
FIG. 2 shows the use of an interbody fusion device filled with micronized composition to fuse two vertebrae.
Figure 3:
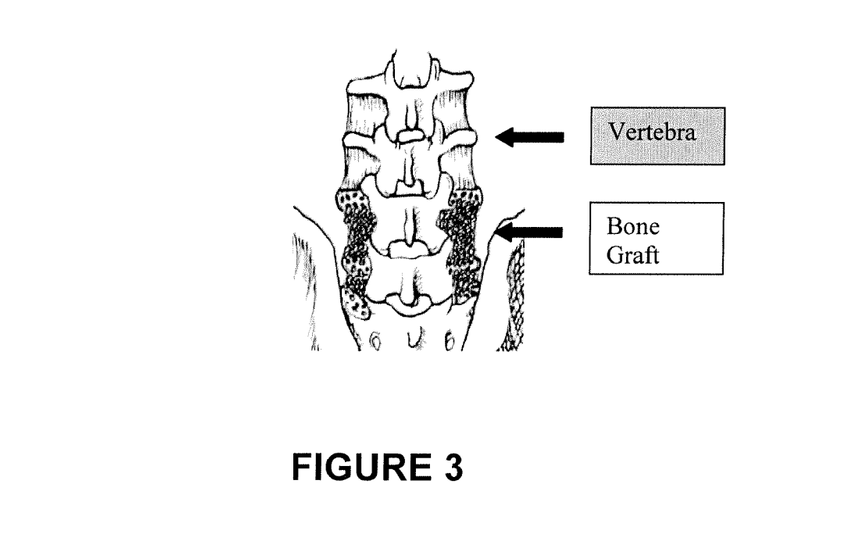
FIG. 3 shows the use of a micronized composition to fuse two vertebrae.

The micronized compositions described herein (i.e., micronized particles with and without the bone grafts) have numerous medical applications. In one aspect, the micronized compositions described herein have numerous orthopedic applications such as, for example, bone void filling, osteochondral repair, bone grafts include interbody fusion, intertransverse process fusion, fresh fractures, non-union fractures, joint reconstruction, tibial metaphysis, foot and ankle fusions, primary and secondary alveolar ridge augmentations, sinus elevations, socket augmentation, site preservation, and periodontal intrabony defects. In one aspect, the micronized compositions can be used to fuse two or more bones together. An example of this is depicted in FIGS. 2 and 3, where a micronized composition is injected into the vertebrae by an interbody fusion device (FIG. 2) to fuse two vertebra (FIG. 3).

The micronized compositions are useful in numerous would healing applications. In one aspect, the micronized compositions described herein are useful for addressing or alleviating complications to the spine and surrounding regions that occur after surgery. In one aspect, the compositions described herein are useful in preventing or reducing scar formation on the spine or near the spine. As discussed above, scar formation at or near the spine after surgery can be very debilitating and possibly require subsequent operations to address the symptoms. The term "anti-adhesion" is also used in the art to refer to the prevention of scar tissue at or near the spine. In other aspects, the micronized compositions described herein can be used as a protective barrier, where the composition protects the spinal dura from post surgical trauma from the surrounding surgical site. For example, the compositions can prevent damage to the spinal dura caused by sharp edges from newly cut bone such as vertebrae.

Depending upon the surgical procedure, the micronized composition can be applied directly to the spinal dura, the surrounding region of the spine to include nerve roots, or a combination thereof. Due to the unique structure of vertebrae, the micronized compositions can be formulated into gels or a paste so that it can be placed and affixed at the appropriate position in the subject. In addition to minimizing lateral movement, the micronized compositions can also provide proximal and distal barrier coverage where the spinal lamina has been removed for exposure to the affected area.

The micronized compositions are useful in preventing or reducing scar formation that can result from a variety of surgical procedures associated with the spine. The compositions can be used after any procedure in the neck, midback, or lower back. For example, the compositions can be used after anterior procedures or modified anterior procedures such as Anterior Lumbar Interbody Fusion (ALIF) and Transforaminal Interbody Fusion (TLIF). In these aspects, the compositions provide additional protection to the vertebral surgical site by maintaining separation from the peritoneum, larger vessels, and abdominal musculature. The composition serves as a reduced friction anatomical barrier against adhesions and scaring. For example, the compositions can prevent scar tissue binding major blood vessels to the spine. This is a common problem with post-spinal surgery, which requires a second surgical procedure to address this.

In another embodiment for preventing or reducing scar formation, the micronized compositions described herein may be used in conjunction with a multilayered tissue graft, such as is described in U.S. provisional application Ser. No. 61/683,698, the content of which is specifically incorporated by reference in its entirety.

Figure 4:
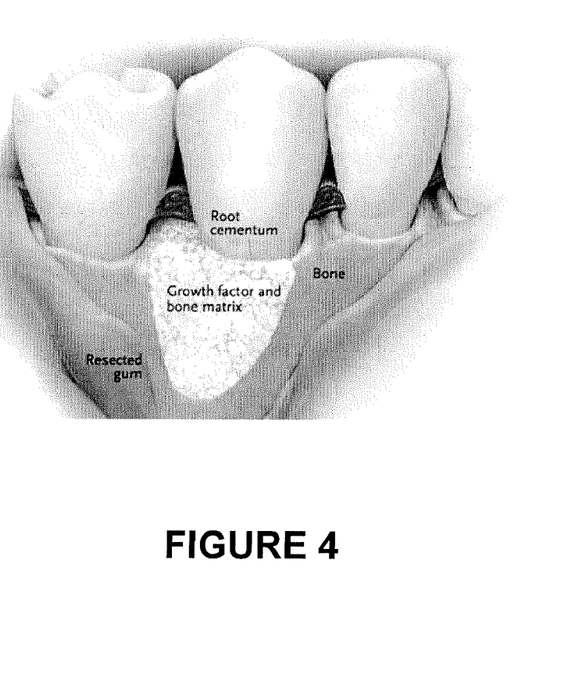
FIG. 4 shows the use of a micronized composition in a dental bone void.

In other aspects, the micronized compositions can be used in dental regenerative procedures including the treatment of gingival recession defects, vertical and horizontal gingival augmentation, increasing the amount of attached gingival tissue, elimination of a frenum pull, augment tissue around dental implants, regeneration of papilla tissue, vestibuloplasty, guided tissue regeneration, guided bone regeneration over grafted extraction sockets, intrabony osseous defects, fenestration and dehiscence osseous defects, primary and secondary ridge augmentations, covering the lateral window of the sinus, and over tears in the Schendiarn membrane. In applications involving oral mucosa tissue including treating mouth sores, oral lesions, and replace larger amounts of mucosa tissue lost through disease or traumatic injury. In another aspect, the micronized compositions can be used as a socket filler after tooth extraction or to fill a dental void. This feature is depicted in FIG. 4, where a void in the jaw of a subject is filled with the micronized composition (40) described herein.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of Micronized Particles

In one aspect, a micronized human amniotic membrane injectable was composed of human amnion as described above and intermediate layer tissue obtained from placental tissue originated in a hospital, where it is collected during a Cesarean section birth. The micronization of the tissue was performed using a Retsch Oscillating Mill MM400. Phosphate buffer was used as a carrier. The ratio of the injectable was 50 mg/mL. The concentration ratio was 60% (21 mg) amnion and 40% (14 mg) intermediate tissue layer with 0.70 mL of phosphate buffer.

Example 2

Preparation of Micronized Compositions

In one aspect, the micronized composition can be prepared as follows: (1) obtaining placental tissue, (2) cleaning of the tissue, (3) dehydration of tissue, (4) pulverize, grind and or mill dehydrated tissue, (5) roll particulate placental tissue to form micronized particles, (6) screen or sift the micronized particles to obtain average particle size of 250 μm, ±50 μm, (7) packing of dry micronized particles into vials, (8) terminal sterilization, and (9) micronized particles are mixed with a bone graft to form a composite graft that is 50% micronized particles and 50% bone graft by volume.

In another aspect, a gel or putty composed of the micronized composition can be produced by: (1) obtaining placental tissue, (2) cleansing of the tissue, (3) dehydration of tissue, (4) pulverize, grind and or mill dehydrated tissue, (5) roll particulate placental tissue to form micronized particles, (6) screen or sift the micronized particles to obtain average particle size of 250 μm, ±50 μm, and (7) combine micronized particles and bone graft at a 1:1 ratio by volume with biocompatible filler such as carboxymethylcellulose, cellulose hyaluronate, or glycerin, to form a gel or paste that is 20-80% micronized composition and 20-80% filler by weight using a sol-gel method. The gel or putty can be packaged into a syringe and further sterilized.

In a further aspect, a foam composed of the micronized composition can be produced by: (1) obtaining placental tissue, (2) cleansing of the tissue, (3) dehydration of tissue, (4) pulverize, grind and or mill dehydrated tissue, (5) roll particulate placental tissue to form micronized particles, (6) screen or sift the micronized particles to obtain average particle size of 250 μm, ±50 μm, and (7) combine micronized particles and bone graft at a 1:1 ratio by volume with biocompatible filler such as carboxymethylcellulose, cellulose hyaluronate, or glycerin, to form a gel or paste that is 20-80% micronized composition and 20-80% filler by weight using a sol-gel method, and (8) freeze drying the slurry to create a composite foam.

Example 3

Preparation of Micronized Compositions with a Bioactive Agent

A micronized composition was prepared according to the steps set forth in Example 2. Specifically, 5 mg of a micronized placental tissue having an average particle size of 10 μm was admixed with a bone graft at a weight ratio of 1:1 to form a composite graft that is 50% micronized particles and 50% bone graft by volume. Next, carboxymethylcellulose and a buffer were added at a weight ratio of 1:1 to form a filler composition suitable for use in bone grafting. Aliquots of the filler composition were then separated into separate containers and various bioactive agents, including an anti-inflammatory agent, an antibiotic and growth factors were added into each separate filler composition to form a series of micronized compositions having a bioactive agent incorporated therein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A micronized placental composition comprising (a) dehydrated micronized particles, selected from the group consisting of micronized placental amnion particles and micronized particles comprising placental amnion and chorion, and (b) one or more bone grafts;
   wherein said dehydrated micronized particles comprise a fibroblast cell layer;
   wherein the one or more bone grafts are independently selected from the group consisting of an autograft, an allograft, a xenograft, and an alloplast, and any combination thereof;
   wherein the amount of said micronized particles to said one or more bone grafts is from 1:99 to 99:1 by volume.

2. The composition of claim 1, said dehydrated micronized particles having a particle size of from 150 μm to 350 μm.

3. The composition of claim 1, wherein the dehydrated micronized particles are 100% micronized placental amnion.

4. The composition of claim 1, further comprising micronized Wharton's jelly.

5. A pharmaceutical composition prepared by admixing the composition of claim 1 with a pharmaceutically-acceptable carrier.

6. The composition of claim 5, wherein the pharmaceutically acceptable carrier comprises water, saline, Ringer's solution, dextrose solution, Hank's solution, a buffer, or a nonaqueous vehicle.

7. The composition of claim 6, wherein the buffer comprises a phosphate buffer, bicarbonate buffer, or Tris buffer.

8. The composition of claim 5, wherein the pharmaceutically acceptable carrier comprises a biocompatible filler.

9. The composition of claim 8, wherein the filler is carboxymethylcellulose, cellulose, hyaluronic acid or a salt thereof, glycerin, or any combination thereof.

10. The composition of claim 1, wherein the composition is injectable.

11. The composition of claim 1, wherein the composition is a foam, gel, putty, or paste.

12. A composition consisting essentially of:
    a. dehydrated micronized placental amnion particles, wherein the micronized placental amnion retains a non-viable fibroblast cell layer; and
    b. one or more bone grafts; wherein the one or more bone grafts are independently selected from the group consisting of an autograft, an allograft, a xenograft, and an alloplast, and any combination thereof;

wherein the amount of the dehydrated micronized placental amnion particles to the one or more bone grafts is from 1:99 to 99:1 by volume.

13. A micronized composition suitable for use in treating a bone defect, the composition consisting essentially of:
(a) dehydrated micronized placental amnion particles, wherein the micronized placental amnion retains a fibroblast cell layer;
(b) one or more bone grafts; wherein the one or more bone grafts are independently selected from the group consisting of an autograft, an allograft, a xenograft, and an alloplast, and any combination thereof;
(c) a pharmaceutically acceptable carrier admixed with (a) and (b), and
(d) a biodegradable filler;
wherein the amount of said dehydrated micronized placental amnion particles to said one or more bone grafts is from 1:99 to 99:1 by volume.

14. The micronized composition of claim 13;
wherein the dehydrated micronized placental amnion particles have a particle size of from 150 μm to 350 μm.

15. The composition of claim 11, wherein the composition is a foam.

* * * * *